US009593075B2

(12) United States Patent
Bruns et al.

(10) Patent No.: US 9,593,075 B2
(45) Date of Patent: Mar. 14, 2017

(54) METHOD FOR PRODUCING ISOCYANATES

(71) Applicant: Bayer Intellectual Property GmbH, Monheim (DE)

(72) Inventors: Rainer Bruns, Leverkusen (DE); Wolfgang Lorenz, Dormagen (DE); Andreas Karl Rausch, Kaarst (DE); Stefan Wershofen, Monchengladbach (DE); Tim Loddenkemper, Dormagen (DE)

(73) Assignee: Covestro Deutschland AG, Kaiser-Wilhelm-Allee, Leverkusen (DE)

( * ) Notice: Subject to any disclaimer, the term of this patent is extended or adjusted under 35 U.S.C. 154(b) by 0 days.

(21) Appl. No.: 14/385,270

(22) PCT Filed: Mar. 15, 2013

(86) PCT No.: PCT/EP2013/055441
§ 371 (c)(1),
(2) Date: Sep. 15, 2014

(87) PCT Pub. No.: WO2013/139703
PCT Pub. Date: Sep. 26, 2013

(65) Prior Publication Data
US 2015/0291512 A1  Oct. 15, 2015

(30) Foreign Application Priority Data
Mar. 19, 2012 (EP) .................... 12160168

(51) Int. Cl.
*C07C 263/10* (2006.01)
*C07C 263/20* (2006.01)

(52) U.S. Cl.
CPC .......... *C07C 263/10* (2013.01); *C07C 263/20* (2013.01); *Y02P 20/582* (2015.11)

(58) Field of Classification Search
CPC ................... C07C 263/10; C07C 263/20
See application file for complete search history.

(56) References Cited

U.S. PATENT DOCUMENTS

| 2,471,134 | A | 7/1946 | Wright |
| 3,713,833 | A | 1/1973 | Lindholm et al. |
| 3,987,075 | A * | 10/1976 | Schnabel .......... C07C 263/20 203/43 |
| 4,118,286 | A * | 10/1978 | Burns ................ C07C 263/20 203/69 |
| 4,289,732 | A | 9/1981 | Bauer et al. |
| 4,419,295 | A | 12/1983 | Hennig et al. |
| 4,847,408 | A | 7/1989 | Frosch et al. |
| 4,851,571 | A | 7/1989 | Sauer et al. |
| 4,915,509 | A | 4/1990 | Sauer et al. |
| 5,391,683 | A | 2/1995 | Joulak et al. |
| 5,449,818 | A | 9/1995 | Biskup et al. |
| 5,925,783 | A * | 7/1999 | Jost ..................... C07C 263/10 560/347 |
| 5,931,579 | A | 8/1999 | Gallus et al. |
| 6,974,880 | B2 | 12/2005 | Biskup et al. |
| 7,358,388 | B2 | 4/2008 | Woelfert et al. |
| 7,524,405 | B2 | 4/2009 | Sohn et al. |
| 7,592,479 | B2 | 9/2009 | Stroefer et al. |
| 7,649,108 | B2 | 1/2010 | Schal et al. |
| 8,088,944 | B2 | 1/2012 | Woelfert et al. |
| 8,273,915 | B2 | 9/2012 | Rumpf et al. |
| 8,546,606 | B2 | 10/2013 | Brodhagen et al. |
| 9,024,057 | B2 | 5/2015 | Biskup et al. |
| 2003/0047438 | A1 | 3/2003 | Tamura et al. |
| 2006/0089507 | A1 | 4/2006 | Sohn et al. |
| 2007/0265465 | A1 | 11/2007 | Keggenhoff et al. |
| 2007/0299279 | A1 | 12/2007 | Pohl et al. |
| 2010/0160673 | A1 | 6/2010 | Bruns et al. |
| 2010/0298596 | A1 | 11/2010 | Keggenhoff et al. |

FOREIGN PATENT DOCUMENTS

| DE | 2844591 A1 | 4/1980 |
| EP | 1371633 A1 | 12/2003 |
| EP | 1371634 A1 | 12/2003 |
| EP | 1413571 A1 | 4/2004 |
| EP | 2210873 A1 | 7/2010 |
| GB | 1165831 | 10/1969 |
| GB | 1238669 | 7/1971 |
| GB | 1263439 | 2/1972 |
| WO | 2010039972 A2 | 4/2010 |

OTHER PUBLICATIONS

Hartung, K.H. et al, Chem. Ing. Techn. 44 (1972), p. 1051 ff.
Danckwerts, P.V., The Definition and Measurement of Some Characteristics of Mixtures, Appl. Sci. Res. (the Hague) A3 (1953), p. 279.
Twitchett, H. J., Chemistry of the Production of Organic Isocyanates, (Chemical Society Reviews (1974), 3(2), pp. 209-230.
Sayigh, A.A.R. et al, The Dehydrochlorination of Allophanoyl Chlorides, A New Synthesis of Isocyanates, Journal of Organic Chemistry (1964), 29(11), pp. 3344-3347.
Stichlmair, Johann, Ullmann's Encyclopedia of Industrial Chemistry, Distillation, 2. Equipment; published online Apr. 15, 2010, DOI: 10.1002/14356007.o08_o01), pp. 456-475.

* cited by examiner

*Primary Examiner* — Paul A Zucker
(74) *Attorney, Agent, or Firm* — Donald R. Palladino

(57) ABSTRACT

The invention relates to a method for preparing isocyanates by phosgenating the corresponding amines, wherein low-boiling secondary components, excess phosgene, and the co-product hydrogen chloride are separated from the crude liquid isocyanate stream, which is obtained after the phosgenation has occurred, within a maximum of 60 minutes, and wherein the crude liquid isocyanate stream is not exposed to temperatures above 250° C. until said separation.

9 Claims, 5 Drawing Sheets

Figure 1B:
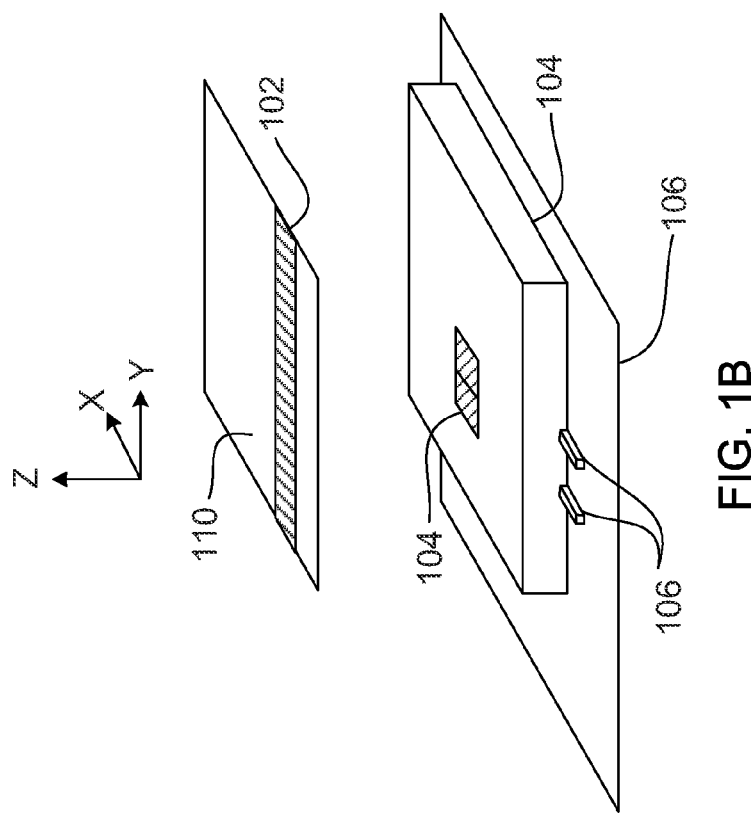
Figure 1A:
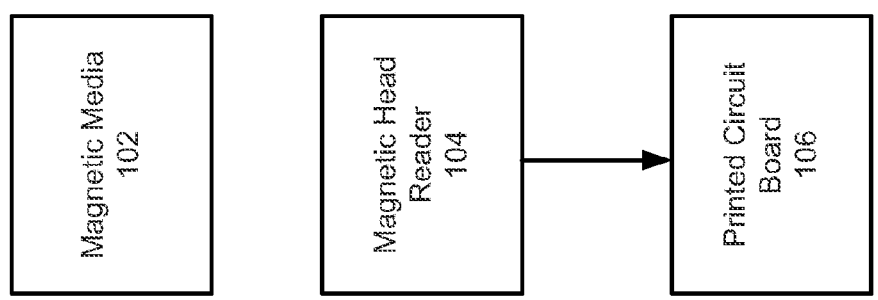
Figure 2B:
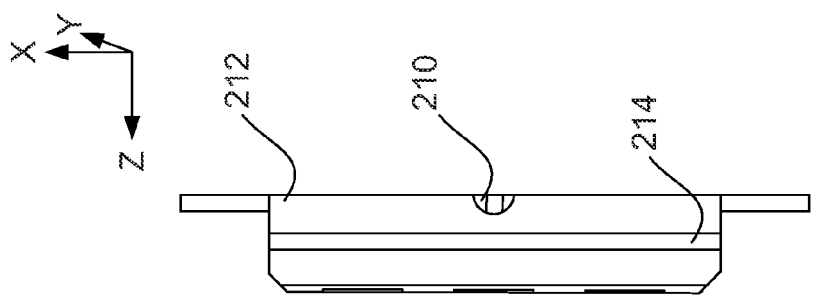
Figure 2A:
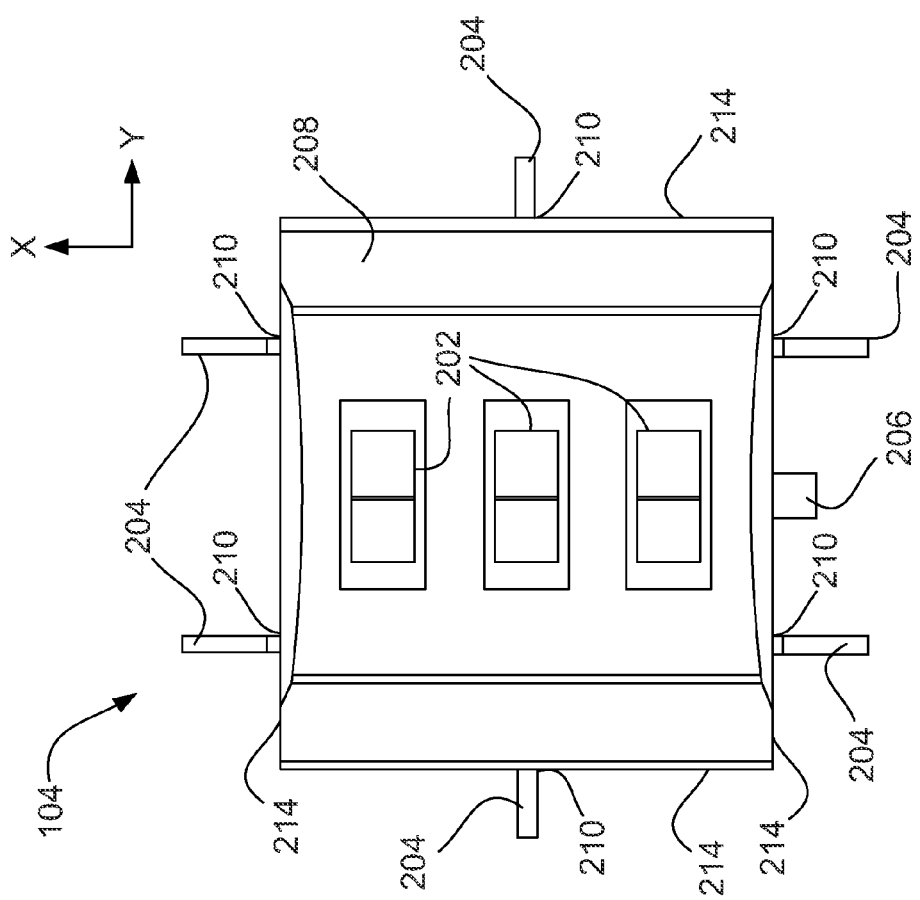
Figure 3A:
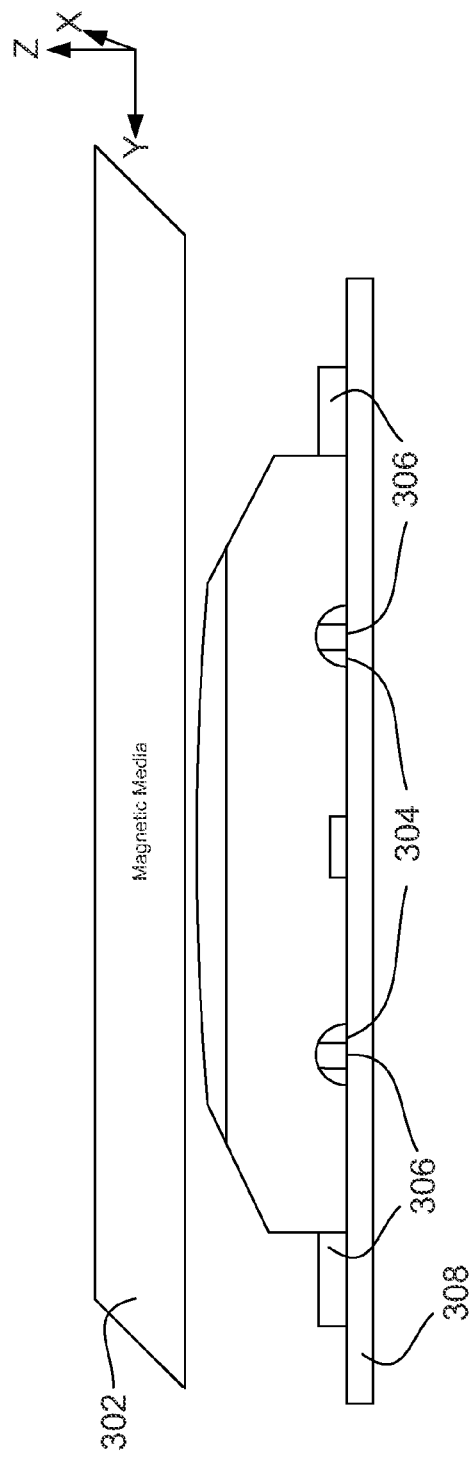
Figure 3B:
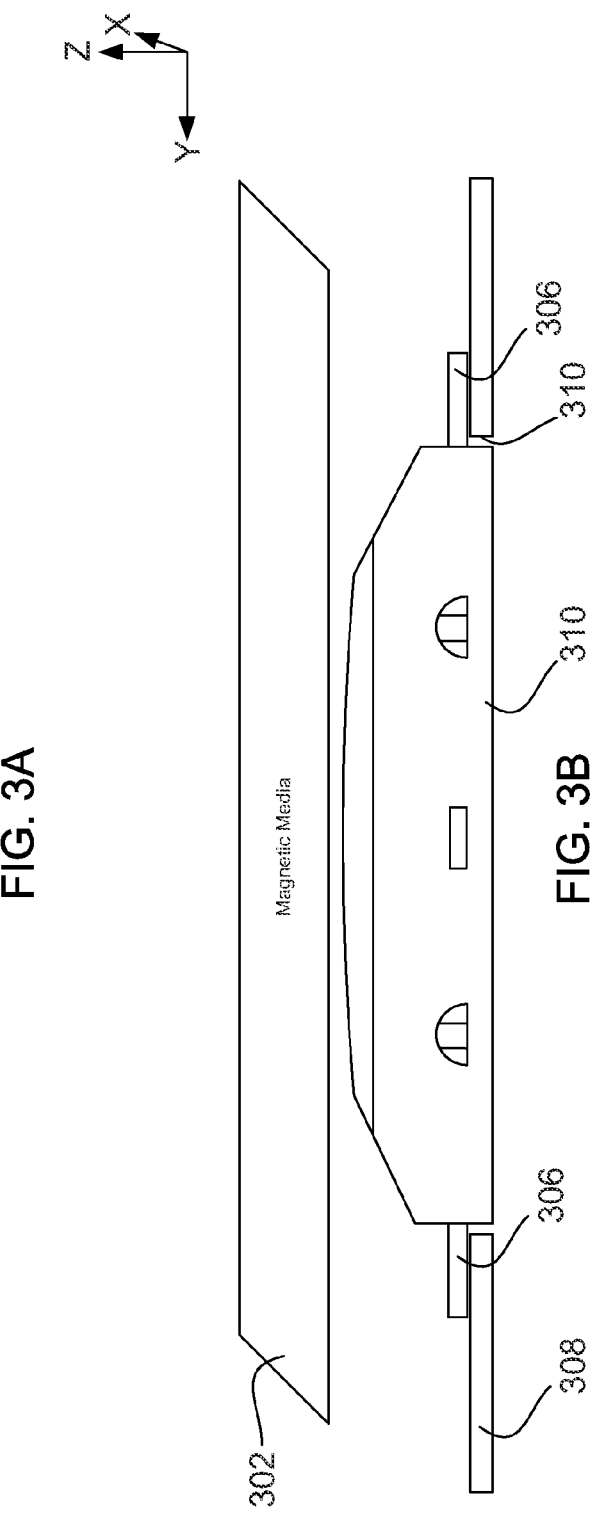
Figure 4:
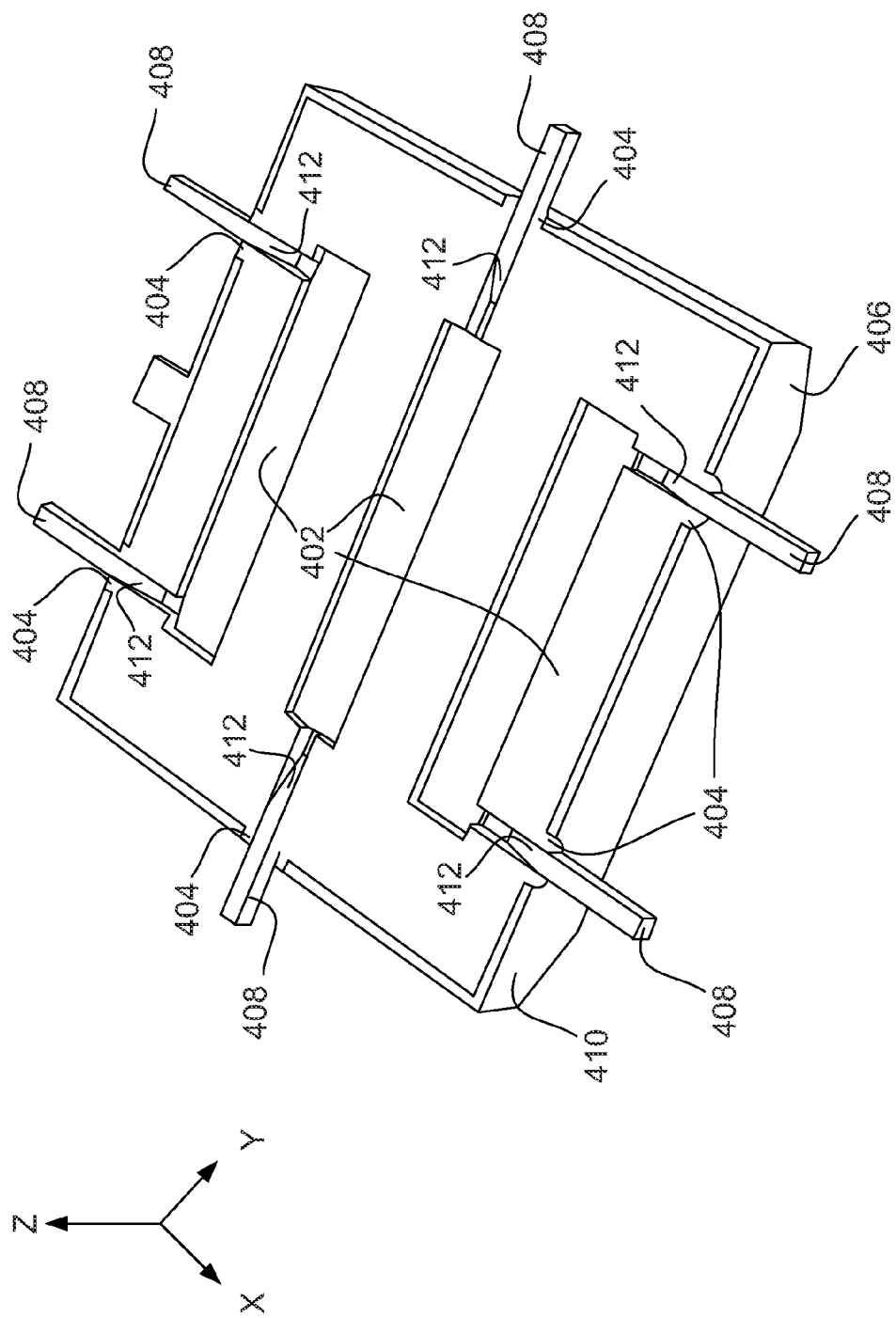

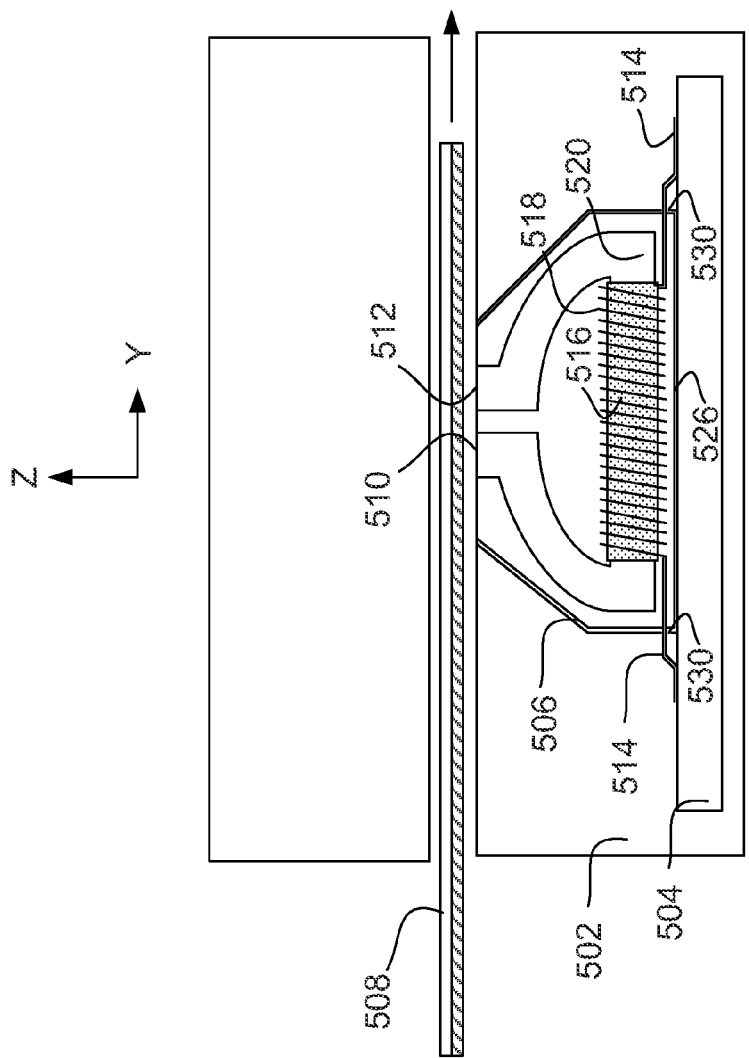
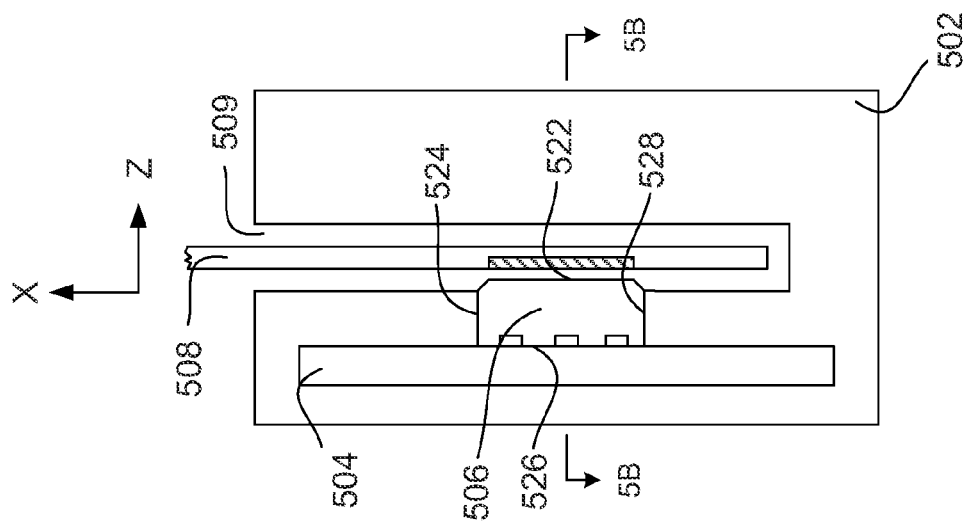
FIG. 5B
FIG. 5A

METHOD FOR PRODUCING ISOCYANATES

The invention relates to a method for preparing isocyanates by phosgenating the corresponding amines, wherein low-boiling secondary components, excess phosgene, and the co-product hydrogen chloride are separated from the crude liquid isocyanate stream, which is obtained after the phosgenation has occurred, within a maximum of 60 minutes, and wherein the crude liquid isocyanate stream is not exposed to temperatures above 250° C. until said separation.

Isocyanates are manufactured in large amounts and mainly serve as starting materials for preparing polyurethanes. They are mostly prepared by reacting the corresponding amines with phosgene, in which, in addition to the isocyanate, hydrogen chloride is also formed.

A common way of manufacturing isocyanates is the reaction of the corresponding amines with phosgene in the liquid phase. This method procedure, also referred to as liquid phase phosgenation (LPP), is characterized in that the reaction is typically conducted in an inert solvent, and that the reaction conditions are selected such that, besides the solvent, at least the amine, isocyanate and phosgene reaction components are at least partially, preferably predominantly, present in the liquid phase under the selected conditions. Some of the hydrogen chloride produced in the reaction as co-product is present dissolved in the liquid phase and some leaves the reactor in gaseous form. The liquid phase phosgenation can be carried out at various temperature and pressure levels. It is possible, for example, to carry out the liquid phase phosgenation at temperatures of 0° C. to 240° C. and pressures of 1 bar to 70 bar; in some cases temperatures up to 300° C. and pressures up to 300 bar are described.

In the liquid phase method, an efficient mixing of amine and phosgene is very important. For this purpose, static (preferably nozzles) and dynamic (comprising mechanically moving parts) mixing devices are used in the prior art. Mixer reactors are known from EP 0 291 819 A and EP 0 291 820 A and EP 0 830 894 A, which consist of a substantially rotationally symmetrical housing, in which the housing has a substantially rotationally symmetrical mixing chamber with separate inlets for the at least two feed streams and one outlet. The inlet for at least one first substance stream is provided in the axis of the mixing chamber and the inlet for at least one second substance stream is configured in the form of a multiplicity of nozzles arranged in rotational symmetry with respect to the mixing chamber axis.

To improve mixing, the mixer reactors also comprise at least one rotor disk-stator disk unit and also an impeller to improve the conveying action in the mixer reactor in favor of a narrow residence time spectrum. It is also possible to dispense with the impeller in the mixer reactors described above. The pressure in the mixing chamber is thereby increased in comparison to the technical teaching of EP 0 291 819 A, EP 0 291 820 A and EP 0 830 894 A. To convey the precursor and/or product stream, the initial pressure of the reactant stream is exclusively used. A pump effect is no longer applied. It is also possible to install a modified inducer in such a way that the conveying action acts against the main conveying direction of the reactant streams or precursor stream. This also causes the pressure in the mixing chamber to increase. The modified inducer is preferably arranged on the same shaft as the rotor disks. Both measures therefore cause an increase in pressure in the mixing chamber in comparison to the technical teaching of EP 0 291 819 A, EP 0 291 820 A and EP 0 830 894 A.

Common to all method variants for liquid phase phosgenation is that the excess phosgene and the hydrogen chloride formed are removed from the crude isocyanate dissolved in the solvent on completion of the reaction. Said removal is generally carried out such that a gaseous stream largely comprising the excess phosgene and hydrogen chloride and a liquid stream, comprising, inter alia, the solvent and the desired isocyanate leaves the reactor in which the reaction takes place. Furthermore, common to all method variants of liquid phase phosgenation is that the gaseous stream is separated into hydrogen chloride and excess phosgene and the latter is generally fed back again to the reaction. The liquid stream comprising the desired isocyanate and the solvent is generally purified by distillation. The liquid stream leaving the reactor still comprises dissolved phosgene and hydrogen chloride according to the prevailing pressure and temperature conditions. These are removed in the distillation, together with reaction secondary components whose formation in the reactor cannot be completely avoided. The desired isocyanate is obtained in high purity by the distillation.

An overview of different variants of the reaction procedure and the workup and product recovery is given in the application documents DE-A-102 60 027, DE-A-102 60 093, DE-A-103 10 888, DE-A-10 2006 022 448, US-A 2007/0299279 and the sources cited therein.

Another possibility for preparing isocyanates is the reaction of the corresponding amines with phosgene in the gas phase. This method procedure, commonly referred to as gas phase phosgenation (GPP), is characterized in that the reaction conditions are selected such that at least the amine, isocyanate and phosgene reaction components, but preferably all reactants, products and reaction intermediates, are gaseous under the selected conditions.

Various methods for preparing di- and/or polyisocyanates by reacting di- and/or polyamines with phosgene in the gas phase are known from the prior art.

GB-A-1 165 831 describes a method for preparing isocyanates in the gas phase in which the reaction of the amine in the vapor phase with the phosgene is carried out at temperatures between 150° C. and 300° C. in a tubular reactor equipped with a mechanical stirrer and temperature-controllable via a heating jacket. The reactor disclosed in GB-A-1 165 831 resembles a thin film evaporator whose stirrer mixes the gases entering the reaction chamber and gases present in the reaction chamber and at the same time covers the surrounding walls of the tubular reactor with the heating jacket in order to prevent a buildup of polymeric material on the tube wall, since such a buildup would hamper the heat transfer. The document does not disclose how the crude isocyanate obtained by the reactor disclosed is purified to the pure isocyanate and how yield losses may be reduced.

EP-A-0 289 840 describes the preparation of diisocyanates by gas phase phosgenation, wherein this document discloses the reaction of the amines with the phosgene in a cylindrical chamber without moving parts in a turbulent flow at temperatures between 200° C. and 600° C. and reaction times of an order of magnitude of 10-4 seconds. According to the teaching of EP-A-0 289 840, the gas streams are introduced into the reactor at one end of the tubular reactor through a nozzle and an annular gap between the nozzle and mixing tube and thereby mixed. According to the teaching of EP-A-0 289 840, it is essential for the viability of the method disclosed therein, that the dimensions of the tubular reactor and the flow rates in the reaction chamber are fixed such that a turbulent flow prevails in the reaction chamber which is characterized by a Reynolds number of at least 2500, preferably at least 4700. According to the teaching of EP-A-0 289 840, this turbulence is generally ensured when the gaseous reaction partner flows through the reaction chamber at a flow rate of more than 90 m/s. The gas mixture leaving the reaction chamber is passed through an inert solvent, which is maintained at a temperature above the decomposition temperature of the carbamoyl chloride corresponding to the diamine, wherein the diisocyanate dissolves in the inert solvent. The document describes that the crude diisocyanate thus obtained can be worked up by distillation, without providing handling instructions for this. The document gives no guideline as to how yield losses and formation of by-products in the crude isocyanate stream can be avoided.

EP-B-0 593 334 discloses a method for preparing aromatic diisocyanates in the gas phase in which a tubular reactor is used. Mixing of the reactants is achieved by a narrowing of the walls. The reaction takes place in a temperature range of 250° C. to 500° C. At the reactor outlet, the reaction product is converted to the liquid phase by supplying solvent. The document describes that the crude isocyanate thus obtained can be worked up by distillation, but handling instructions for this are not given. The document does not disclose any methods in which yield losses can be avoided or reduced during workup of the crude isocyanate.

EP-A-0 570 799 relates to a method for preparing aromatic diisocyanates characterized in that the reaction of the related diamine with the phosgene is carried out in a tubular reactor above the boiling point of the diamine within a mean contact time of the reactants of 0.5 to 5 seconds. As described in the document, reaction times that are too long or too short both lead to undesirable solids formation. Therefore, a method is disclosed in which the average deviation from the mean contact time is less than 6%. It is also disclosed in this method that a liquid phase comprising, inter alia, crude isocyanate and a gaseous phase comprising phosgene and hydrogen chloride is obtained by using a solvent at the outlet of the reactor. The document does not provide handling instructions for purification of the crude isocyanate.

Compliance with the disclosed contact time distribution is achieved firstly by the fact that the reaction is carried out in a flow tube which is characterized either by a Reynolds number of over 4000 or a Bodenstein number above 100. According to the teaching of EP-A-0 570 799, a plug flow up to approximately 90% is thereby achieved; furthermore, all parts by volume of the stream have substantially the same flow times such that the lowest possible deviation in the contact time distribution between the reaction partners occurs due to the approximately uniform residence times of all parts by volume.

However, according to the teaching of EP-A-0 570 799, the deviation in the mean contact time in the practical performance of the method is also largely determined by the time required for mixing the reaction partners. EP-A-0 570 799 states that, as long as the reaction partners are not homogeneously mixed, volumes of gas are still present in the reaction chamber which were not able to come into contact with the reaction partner and therefore different contact times of the reaction partners are obtained depending on the mixing of the parts by volume at uniform flow times. According to the teaching of EP-A-0 570 799, the mixing of the reaction partners should occur within a period of 0.1 s to 0.3 s up to a degree of segregation of $10^{-3}$, where the degree of segregation serves as a measure of the incompleteness of the mixing (see e.g. Chem. Ing. Techn. 44 (1972), p. 1051 ff; Appl. Sci. Res. (the Hague) A3 (1953), p. 279). EP-A-0 570 799 discloses that, to obtain appropriately short mixing times, known methods based on mixing units having moving or static mixing devices, preferably static mixing devices, may in principle be used, while according to the teaching of EP-A-0 570 799 in particular, use of the jet mixer principle affords sufficiently short mixing times.

A liquid stream comprising, inter alia, the crude diisocyanate, in addition to the solvent used to liquefy the product gas stream and optionally to stop the reaction, and also a gaseous stream largely comprising excess phosgene and hydrogen chloride is therefore also obtained in the gas phase phosgenation on completion of the reaction. The gaseous stream is generally separated into hydrogen chloride and phosgene and at least part of the phosgene is reused in the reaction. The liquid stream comprising the desired isocyanate, inter alia, leaving the reactor, is generally purified by distillation to obtain pure isocyanate.

The essential difference in the methods between the liquid phase phosgenation and the gas phase phosgenation is, therefore, the reaction conditions in the reactor. Common to both variants of the method for preparing isocyanates is that, on completion of the reaction, firstly a crude product comprising the desired isocyanate, inert solvent, secondary components, hydrogen chloride and unreacted phosgene is obtained, which is split into a gaseous and a liquid product stream, where the liquid product stream comprises, inter alia, the solvent and the crude isocyanate and this liquid stream is generally worked-up by distillation.

Despite significant improvements in the reactions both in the liquid phase and the gas phase phosgenation, both by improved mixing techniques and improved reaction procedures, the formation of high boiling and low boiling reaction secondary components in the reaction is not completely avoided. In the context of the present invention, all substances or azeotropically boiling substance mixtures whose boiling points are below that of the desired isocyanate in the context of the prevailing conditions of pressure and temperature, are referred to as "low boilers". All substances or azeotropically boiling substance mixtures whose boiling points are above that of the desired isocyanate in the context of the prevailing conditions of pressure and temperature, are referred to as "high boilers". In the context of the present invention, therefore, "low boilers" applies to the co-product hydrogen chloride and unreacted phosgene. In the context of the present invention, reaction secondary components (i.e. the products of undesired side reactions) are referred to as "low boilers" if they fulfill the definition of "low boilers" mentioned above, and are referred to as "high boilers" if they fulfill the definition of "high boilers" mentioned above. The solvent—either already used in the reaction or not added until later—usually falls into the group of low-boiling substances (but it is not considered as a "low boiler" in the above sense since it is not a reaction secondary component). However, it is also possible to use a solvent which is assigned to the group of high-boiling substances (but it is not considered as a "high boiler" in the above sense since it is not a reaction secondary component).

In addition to the side reactions occurring in the reactor in both methods, side reactions are also observed which may take place in the liquid product stream comprising the crude isocyanate leaving the reactor. This stream leaving the reactor also respectively comprises hydrogen chloride and excess phosgene in addition to the crude isocyanate, solvent, low boilers and high boilers. In particular, phosgene is a highly reactive molecule which may react further with other components of the liquid product stream until the separation.

A fundamental problem is that relatively long residence times occur in the course of the workup to obtain the pure isocyanate, which encourages high boiler formation from the isocyanate material of value. Furthermore, high boiling secondary components already produced in the reaction pass into the workup, whereby a further high boiler formation from the isocyanate material of value is encouraged. These secondary components have the property of reacting with the isocyanates and therefore to reduce the proportion of isocyanates in an isocyanate/secondary component mixture as is obtained in a phosgenation reactor. This leads to the formation of residues which are enriched in high boiling secondary components. The difficult handling qualities and the typical composition of such a residue are cited, for example, in DE-A-102 60 093.

In WO 2004/056759 A1, for example, the two-stage separation of isocyanates from an isocyanate/high boiler mixture (stream 1) is described. Stream 2 (bottom) and 3 (distillate) are distributed in a weight ratio of 20:1 to 1:1. In other words, at most 50% of stream 1 are drawn from the bottom. The solution is concentrated, pumped into a kneader dryer and further evaporated therein.

According to WO 2009/027418 A1, the yield losses mentioned can be reduced if the high boiling compounds already present in the crude isocyanate mixture, such as urea and its conversion products produced by phosgenation or species formed by secondary reactions of isocyanate, e.g. carbodiimide, isocyanurate, uretdione, are separated before or during the actual distillation sequence for removal of the solvent and the low boilers using a suitable apparatus concept. It has also been found that some of the high boiling components comprising the isocyanate can be dissociated back into the isocyanate by suitable pre-evaporation, whereby yield losses via the bottom effluent of the distillation column can be reduced. Furthermore, it is thereby avoided that monomeric isocyanate attaches to the high boiling compounds during the workup and the yield is thereby reduced. The remaining bottom products comprise carbodiimides present mainly in polymeric form and polynuclear chlorinated secondary components as major constituents.

From the compilation of various patent applications above, it is evident that the process variants described therein relate either to suitable apparatus or process operations in the phosgenation reaction and the provision/supply of reactants or concern variants of the process operations in the workup of the reaction mixture including the separation of low boilers, solvent and/or high boilers. All measures described should serve to enable a stable process operation or to avoid or reduce the formation of yield-reducing secondary components Despite the many efforts already made to optimize the reaction of amines with phosgene, there still exists a need to improve this phosgenation reaction with respect to reducing secondary components. In this context, little attention has been paid to date to the reaction section between the reaction and the removal of low-boiling substances and solvent. It has now been found, surprisingly, that this method section has a pronounced influence on the process operation, particularly from the point of view of safety, product quality and cost-effectiveness of the method.

The improvement of the method according to the invention for phosgenating amines requires an understanding of the correlations between some of the side reactions occurring which are therefore explained in more detail below.

For example, two reaction pathways are important for the formation of carbodiimides. Firstly, the thermal decomposition of isocyanates may be mentioned, in which two isocyanate groups react with each other with elimination of CO2. This reaction can occur at all stages of the process in which isocyanate is present at elevated temperatures.

Secondly, according to H. J. Twitchett (Chemical Society Reviews (1974), 3(2), 209-230), the phosgenation of ureas formed as secondary components in the phosgenation lead not only to the corresponding isocyanates but also to carbodiimides; in addition, the formation of various chlorine-containing structural elements is also possible, e.g. chloroformamidines, chloroformamidine-N-carbonylchloride and/or isocyanide dichlorides, which arise along the reaction pathway as intermediates. Since, by improving the reaction procedure both in the liquid and in the gas phase phosgenation, the formation of ureas is generally only of minor importance, this formation of the carbodiimide pathway plays only a minor role. Nevertheless, the formation of urea and the resulting carbodiimide formation in the presence of phosgene cannot be completely excluded.

Chloroformamidine may also be formed from carbodiimides by (reversible) addition of hydrogen chloride, which, for example, is present in the reaction mixture of the phosgenation (see e.g.: A. A. R. Sayigh, J. N. Tilley, H. Ulrich, Journal of Organic Chemistry (1964), 29(11), 3344-3347) and may in turn further react thermally, for example, to give trisubstituted guanidine hydrochlorides. Similarly, chloroformamidine-N-carbonyl chlorides are formed from carbodiimides by the (reversible) addition of phosgene, which, for example, is present in the reaction mixture of the phosgenation (see e.g.: H. J. Twitchett, Chemical Society Reviews (1974), 3(2), 209-230) and can be thermally cleaved again into carbodiimides and phosgene.

The reactions presented, namely thermal carbodiimide formation and carbodiimide formation by phosgenation of urea and also the subsequent reaction of carbodiimides with hydrogen chloride and/or phosgene to give by-products may take place both in the reactor and also in the liquid product stream comprising the crude isocyanate leaving the reactor, since in this stream certain amounts of hydrogen chloride and phosgene are always dissolved according to the prevailing pressure and temperature conditions at the outlet of the reactor. The subsequent reactions with hydrogen chloride and phosgene are also possible in the workup and distillation stages if they are not largely removed from the liquid product stream comprising the crude isocyanate.

Despite large excesses of phosgene, good mixing technique and the measures already discussed from the prior art, the formation of by-products with urea structures in the reactor cannot be completely ruled out. Since a possible subsequent reaction of ureas leads to carbodiimide formation, the liquid product stream comprising the crude isocyanate leaving the reactor also always comprises carbodiimide fractions. The reaction of these carbodiimides with excess phosgene therefore always leads to certain proportions of secondary components having chloroformamidine-N-carbonyl chloride structural elements. This reaction inevitably proceeds, particularly in the liquid phase in the presence of dissolved phosgene, as long as phosgene is still present dissolved in the liquid phase.

It is not only the early removal of high boilers that is helpful to minimize yield losses as described in the literature according to the prior art. Also low-boiling substances present in the liquid product stream comprising the crude isocyanate, such as low boilers and particularly the co-product hydrogen chloride and unreacted phosgene, can lead to yield reductions.

The formation of secondary components, including the carbodiimides mentioned above and the chlorine-containing species, causes yield losses and thus economic disadvantages. If chlorine-containing species get into the process product, this leads moreover to undesirable elevated chlorine levels in the product. In addition, by-products having phosgene carrier chloroformamidine-N-carbonyl chloride structural elements which may get into virtually phosgene-free phases of the method and eliminate phosgene again under thermal stress, whereby phosgene can get into virtually phosgene-free phases of the method.

Mindful of the problems mentioned above, the present invention is concerned with providing a method for preparing isocyanates from the corresponding amines which is characterized by a low tendency to form secondary components, which may lead to losses in yield and/or quality issues and/or phosgene development in virtually phosgene-free phases of the method.

The invention therefore relates to a continuous method for preparing an isocyanate by
(i) reacting the corresponding primary amine with phosgene in stoichiometric excess in a reaction chamber, wherein the reaction is carried out either
in the liquid phase in the presence of an inert solvent or
in the gas phase, wherein a stream comprising a liquid inert solvent is added to the process product after leaving the reaction chamber,
such that a crude product 1 is obtained comprising the desired isocyanate, inert solvent, secondary components having a boiling point below that of the isocyanate (low boilers), secondary components having a boiling point above that of the isocyanate (high boilers), hydrogen chloride and unreacted phosgene,
(ii) separating the crude product 1 into a liquid product stream 2 containing the desired isocyanate and into a gaseous product stream 3,
(iii) working-up the liquid product stream 2, wherein inert solvent, low boilers, high boilers, hydrogen chloride and phosgene are removed from the desired isocyanate,
wherein the low boilers, the hydrogen chloride and the phosgene are removed in step (iii) within a period of 30 seconds to 60 minutes, preferably 60 seconds to 50 minutes, particularly preferably 2 minutes to 40 minutes, following the separation of the crude product 1 in step (ii) into the product streams 2 and 3, and the temperature of the product stream 2 is always maintained below or equal to 250° C., preferably between 100° C. and 250° C., particularly preferably between 120° C. and 230° C.

Preferred primary amines are those selected from the group consisting of aliphatic amines (preferably 1,6-diaminohexane, methylamine, ethylamine, propylamine, butylamine, pentylamine and hexylamine, particularly preferably 1,6-diaminohexane), cycloaliphatic amines (preferably cyclohexylamine, isophorone diamine, 4,4'-diaminodicyclohexyl methane, 2,4'-diaminodicyclohexylmethane, 2,2'-diaminodicyclohexylmethane and mixtures of diaminodicyclohexylmethane isomers, particularly preferably isophorone diamine, 4,4'-diaminodicyclohexylmethane, 2,4'-diaminodicyclohexylmethane, 2,2'-diaminodicyclohexylmethane and mixtures of diaminodicyclohexylmethane isomers), araliphatic amines (preferably benzylamine), and aromatic amines (preferably aniline, chloroaniline, toluylenediamine, 1,5-diaminonaphthalene, 4,4'-diaminodiphenylmethane, 2,4'-diaminodiphenylmethane, 2,2'-diaminodiphenylmethane, mixtures of diaminodiphenylmethane isomers and mixtures of diaminodiphenylmethane isomers and higher homologues thereof [also generally referred to as e.g. MDA, PMDA, polymer-MDA or di- and polyamines of the diphenylmethane series, i.e. mixtures of di- and polyamines, which are obtained from the acid-catalyzed condensation of aniline and formaldehyde], particularly preferably toluylenediamine).

The primary amine used in the method according to the invention is especially preferably toluylenediamine (TDA). TDA is generally obtained by nitration of toluene to give dinitrotoluene (DNT) and subsequent hydrogenation thereof. An isomeric mixture is preferably used which is largely composed of meta-TDA isomers (m-TDA; i.e. the two amino groups are in the meta position to each other) and comprises from 78% by weight to 82% by weight 2,4-TDA and from 18% by weight to 22% by weight 2,6-TDA, and which may comprise less than 1% by weight of the para-TDA isomer (2,5-TDA). In the method according to the invention for reacting aromatic diamines with phosgene, however, the use of isomeric mixtures of m-TDA with isomeric ratios deviating therefrom and also the separate use of technically pure 2,4- or 2,6-TDA isomers is also possible. The TDA may potentially also comprise low amounts of impurities.

Reaction in stoichiometric excess is understood to mean that more than the calculated amount of phosgene is used based on the underlying stoichiometry of the reaction equilibrium. The molar excess of phosgene, based on the primary amino groups present, is preferably between 1.0% and 1000%, particularly preferably between 10% and 500% and especially preferably between 50% and 350% of theory.

Reaction chamber is here understood to mean the space in which the conditions for a reaction of primary amine (or intermediates such as e.g. ureas) with phosgene to the desired isocyanate or to a mixture of the desired isocyanate and the corresponding carbamoyl chloride are provided (in the presence of hydrogen chloride, isocyanate and carbamoyl chloride are basically in equilibrium with each other). The reaction chamber therefore begins at the point at which amine and phosgene are brought into contact with each other for the first time under conditions which enable a reaction. The reaction chamber stops in the case of the liquid phase reaction at the point at which the reaction is terminated by introducing suitable measures (e.g. lowering the temperature). The reaction chamber is typically defined by the spatial dimensions of the interior of the apparatus used.

The reaction chamber stops in the case of the gas phase reaction at the point at which either the gas stream composed of products, secondary components, any unreacted reactants and intermediates and optionally added inert substances is fed into a device for liquefying the isocyanate formed or the reaction is terminated by introducing other suitable measures (e.g. lowering the temperature).

The reaction chamber is located in both method procedures in a technical device for carrying out chemical reactions, i.e. the reactor. A plurality of reactors, connected in parallel or in series, may also be used. In the simplest case, the reaction chamber is identical with the interior volume of the reactor or reactors. It is also conceivable that a reactor comprises a plurality of reaction chambers.

Reaction in the liquid phase is understood to mean that the amines react in the liquid phase to the isocyanates and in the course of the reaction all of the components present (reactants, products, intermediates, possibly secondary components, possibly inert substances), while passing through the reaction chamber, remain in the liquid phase to at least 40.0% by weight, preferably at least 55.0% by weight, particularly preferably 65.0% by weight and especially preferably at least 80.0% by weight, based in each case on the total weight of all the components present in the reaction chamber. A gas phase, if present, is largely composed of HCl and phosgene.

Reaction in the gas phase is understood to mean that the amines react in the gaseous state to the isocyanates and in the course of the reaction all of the components present (reactants, products, intermediates, possibly secondary components, possibly inert substances), while passing through the reaction chamber, remain in the gas phase to at least 95.0% by weight, preferably at least 98.0% by weight, particularly preferably at least 99.0% by weight and especially preferably at least 99.9% by weight, based in each case on the total weight of all the components present in the reaction chamber.

Inert solvents—applicable to the gas and liquid phase reaction—are those which do not react to a significant degree, preferably not at all, with the components present (reactants, products, intermediates, secondary components and/or co-products) under the prevailing conditions of temperature and pressure (see below for details). The inert solvent is preferably selected from at least one solvent from the group consisting of chlorinated aromatic hydrocarbons (preferably chlorobenzene, dichlorobenzene and trichlorobenzene), aromatic hydrocarbons (preferably toluene, xylene and benzene), ethers (preferably diphenyl ether), sulfoxides (preferably dimethylsulfoxide) and sulfones (preferably sulfolane). Particular preference is given here to chlorinated aromatic hydrocarbons. Very particular preference is given to ortho-, meta- or para-dichlorobenzene and also isomeric mixtures of dichlorobenzene. Exceptionally particular preference is given to ortho-dichlorobenzene.

The method according to the invention, surprisingly, is characterized by a low tendency to form secondary products which may lead to yield losses and/or quality issues and/or phosgene development in virtually phosgene-free phases of the method.

In the method according to the invention, the proportion of chlorine-containing species is at least significantly reduced in the product stream obtained after the removal as far as possible of low boilers, hydrogen chloride and phosgene. This also applies to the by-products having chloroformamidine-N-carbonyl chloride structural elements already mentioned, which can get into the virtually phosgene-free phases of the method as phosgene carrier and eliminate phogene again under thermal stress. Since the formation of by-products having chloroformamidine-N-carbonyl chloride structural elements is reduced as far as possible in the method according to the invention, this avoids that phosgene gets into virtually phosgene-free phases of the method.

Embodiments of the present invention are described in detail below, where the individual embodiments may be freely combined with one another, unless it is clearly implied to the contrary from the context. In addition, the liquid phase and gas phase processes are described below. Which of the two method variants is to be preferred depends particularly on the amine to be used. Amines having a very high boiling point, wherein decomposition reactions are to be expected on evaporation, are preferably reacted by the liquid phase method. Amines which can evaporate without decomposition can basically be reacted by both methods. The choice between liquid and gas phase methods in these latter cases is dependent on various factors, not just technical, such as economic constraints. The gas phase method is particularly preferred for the amines selected from the group consisting of 1,6-diaminohexane, methylamine, ethylamine, propylamine, butylamine, pentylamine, hexylamine, cyclohexylamine, isophorone diamine, diaminodicyclohexylmethane (all isomers), mixtures of diaminodicyclohexylmethane isomers, benzylamine, aniline, chloroaniline, toluylenediamine (all isomers), 1,5-diaminonaphthalene and diaminodiphenylmethane (all isomers).

The following description is based primarily on the amine toluylenediamine. For those skilled in the art, it is easy to adjust the method details given below, if necessary, to other amines.

The reaction of toluylenediamine with phosgene in step (i) may either be carried out by the liquid phase or the gas phase methods. The gas phase method is very particularly preferred in the case of toluylenediamine.

In the liquid phase method, the toluylenediamine is optionally already dissolved in one of the inert solvents defined above and is supplied to the reaction chamber at temperatures of −10° C. to 220° C., preferably 0° C. to 200° C., particularly preferably 20° C. to 180° C. The phosgene may be fed to the reaction chamber, either without solvent or also dissolved in one of the inert solvents defined above, at temperatures of −40° C. to 200° C., preferably −30° C. to 170° C., particularly preferably −20° C. to 150° C. The TDA and phosgene, optionally already dissolved in one of the inert solvents defined above, are preferably mixed in the liquid phase method by means of a static mixer or a dynamic mixer. Examples of suitable static mixers are, inter alia, nozzles or nozzle arrangements described in, for example, DE 17 92 660 A, U.S. Pat. No. 4,289,732 or U.S. Pat. No. 4,419,295. Examples of suitable dynamic mixers are, inter alia, pump-like devices such as centrifugal pumps (cf. U.S. Pat. No. 3,713,833) or special mixer reactors (cf. EP 0 291 819 A, EP 0 291 820 A, EP 0 830 894 A).

In the liquid phase method, the reaction is carried out in the reaction chamber at temperatures of 0° C. to 250° C., preferably 20° C. to 200° C., particularly preferably 20° C. to 180° C., with mean residence times of the reaction mixture in the reaction chamber of between 10 s and 5 h, preferably between 30 s and 4 h, particularly preferably between 60 s and 3 h, and at an absolute pressure of at most 100 bar, preferably 1.0 bar to 70 bar, particularly preferably 1.0 bar to 50 bar. Examples of method procedures which can be used according to the invention with respect to the reaction in the reaction chamber are described, for example, in US-A 2007/0299279 (particularly p. 7 paragraphs [0070], [0071], [0089]) and DE-A 103 10 888 (particularly p. 5 paragraphs [0038], [0039]) and documents cited therein.

In the gas phase method, the toluylenediamine is initially converted into the gas phase. This is preferably effected by means of an evaporator as is known from the prior art. The TDA is heated to 200° C. to 600° C., preferably 200° C. to 500° C., particularly preferably 250° C. to 450° C., optionally with an inert gas such as N2, He, Ar or diluted with the vapor of one of the inert solvents defined above and fed to the reaction chamber. In the gas phase method, the phosgene, optionally diluted with an inert gas such as N2, He, Ar or with the vapor of one of the inert solvents defined above, is fed to the reaction chamber in gaseous form at temperatures of 200° C. to 600° C., preferably 200° C. to 500° C., particularly preferably 250° C. to 450° C. The TDA and phosgene are preferably mixed in the gas phase by means of static or dynamic mixing devices known to those skilled in the art. The use of nozzles is preferred, such as is described in EP 1 449 826 B1, particularly in p. 4 paragraphs [0024], [0025], [0026] and p. 5 paragraph [0027], or in EP 2 199 277 B1 in p. 4 paragraphs, [0017], [0018] and p. 5 paragraph [0019].

The reaction in the reaction chamber is effected in the gas phase method at temperatures of 200° C. to 700° C., preferably 200° C. to 650° C., particularly preferably 250° C. to 600° C. and with mean residence times of the reaction mixture in the reaction chamber between 0.01 s and 120 s, preferably between 0.01 s and 30 s, particularly preferably between 0.05 s and 15 s, and at an absolute pressure of at most 5 bar, preferably 0.5 bar to 3.0 bar, particularly preferably 1.0 bar to 2.0 bar. After leaving the reaction chamber, the hot gaseous reaction mixture is cooled by injecting, or passing through, one of the inert solvents defined above at a temperature of 100° C. to 200° C., preferably 150° C. to 180° C., and the isocyanate is liquefied. Examples of method procedures which can be used in accordance with the invention are described, inter alia, in EP 1 449 826 A1 (particularly p. 3 paragraphs [0012], [0017], [0018], p. 4 paragraph [0022] and EP 2 199 277 A1 (particularly p. 8 paragraphs [0054], [0055], [0056], [0057]).

In step (ii), the crude product 1 obtained in (i), comprising the desired isocyanate, inert solvent, low boilers, high boilers, hydrogen chloride and unreacted phosgene, is separated into a liquid product stream 2 and a gaseous product stream 3, which largely comprises hydrogen chloride and excess phosgene. This is preferably carried out in apparatus and containers known to those skilled in the art which are suitable for separating gas and liquid phases. Preference is given to using gas and liquid separators such as cyclone separators, baffle separators, gravitational separators with or without static separation aids.

The liquid product stream 2 obtained in step (ii) comprises, in addition to the isocyanate and the inert solvent used, low-boiling substances such as phosgene and hydrogen chloride, and also high boilers and low boilers. The liquid product stream 2 generally comprises between 10% by weight and 100% by weight of toluylene diisocyanate, between 0% by weight and 90% by weight of inert solvent, between 0% by weight and 5.0% by weight of high boilers, between 10% by weight and 5.0% by weight of low boilers, between 0% by weight and 5.0% by weight of phosgene and between 0% by weight and 5.0% by weight of dissolved hydrogen chloride, based in each case on the total weight of the liquid product stream 2.

Depending on the configuration of step (ii), a plurality of substreams 2a, 2b, etc. may also be obtained, preferably two substreams, 2a and 2b, are obtained. This is the case when the crude product 1 is initially passed into a device for separating gas and liquid phases, wherein a liquid phase 2a and a gas phase is formed, and the gas phase is subsequently passed through a device for droplet separation, where a liquid phase 2b and a gas phase 3 freed of entrained droplets is formed. The additional stream 2b preferably comprises 0% by weight to 5.0% by weight of isocyanate, 0% by weight to 10% by weight of phosgene and 0% by weight to 100% by weight of solvent. The composition of the main stream 2a preferably corresponds to the composition of 2 mentioned above.

If just one liquid product stream 2 is obtained in step (ii), this is processed to give pure isocyanate in step (iii). If two or more liquid product streams 2a, 2b, etc. are obtained in step (ii), these are either combined and processed together to pure isocyanate, or these are partially combined and processed further in two or more substreams, or each substream is further processed separately, wherein at least one of the substreams is processed to pure isocyanate. It is also possible here to combine the substreams at a later time point in the course of their further processing. The requirements of the present invention for the period up to the separation of the low boilers, hydrogen chloride and phosgene and the temperature in step (iii) apply equally to each of the product streams 2a, 2b, etc.

The description of step (iii) below is based on the embodiment with exactly one liquid product stream 2. The method details apply analogously, however, to the processing of multiple substreams 2a, 2b, etc., with optional adjustments self-evident to those skilled in the art.

The temperature of the liquid product stream 2 obtained in step (ii) is generally at most 250° C., preferably at most 220° C. and particularly preferably at most 200° C. Furthermore, the temperature of 2 is typically at least 60° C., preferably at least 90° C. and particularly preferably at least 110° C. These values apply equally to the liquid and the gas phase methods.

Furthermore, a gaseous product stream 3 largely comprising phosgene and hydrogen chloride is obtained in step (ii). The composition of this stream depends on the exact process parameters in step (i) and (ii). Detailed knowledge of the composition of 3 is not relevant for understanding the invention. In the context of the present invention, the product stream 3 is further processed as is customary from the prior art. Among other things, phosgene is separated and recycled in the process. Hydrogen chloride is also separated and purified as required in order to be able to use it, for example, as aqueous hydrochloric acid after absorption, or to close the chlorine circuit, in which hydrogen chloride, for example, is reconverted to chlorine by means of electrolysis or by oxidation in a Deacon process.

The workup of the liquid product stream 2 in step (iii) is preferably carried out by distillation. Alternatively, other methods, such as crystallization, extraction or membrane methods may also be used for the workup. Of course, a combination of various methods for the workup is also possible.

The preferred workup by distillation of the liquid product stream 2 in step (iii) may be carried out either in a single stage or particularly preferably in multiple stages. Suitable apparatuses are, for example, columns which are optionally provided with suitable internals and/or random packings, separating trays and/or structured packings. Preference is given to dividing wall columns. Suitable combinations of multiple columns or column types are also possible. Using a dividing wall column, two or more separation processes and tasks for the workup may be combined in one apparatus. In general, the workup by distillation is conducted at bottom temperatures in the range of 60° C. to 250° C., preferably 100° C. to 240° C., and particularly preferably 120° C. to 230° C. The absolute head pressures are generally in the range of 1.0 mbar to 1400 mbar, preferably 5.0 mbar to 1013 mbar. The absolute bottom pressures are higher than the head pressures and are in the range of 2.0 mbar to 2000 mbar, preferably 7.0 mbar to 1500 mbar.

The workup in step (iii), preferably by distillation, comprises obtaining the product of value toluylene diisocyanate (TDI) by removing the inert solvent, the low boilers, the high boilers, the phosgene and the hydrogen chloride. The inert solvent is preferably purified as required and recycled into the process. Hydrogen chloride may also be present chemically bound, e.g. as carbamoyl chloride and also in the form of other chlorine-containing species. The species with chemically bound hydrogen chloride are generally in the group of the high boilers. Carbamoyl chloride in step (iii) is cleaved as far as possible to obtain the isocyanate.

It is essential to the invention that the low boilers, the hydrogen chloride and the phosgene in step (iii) are removed from the desired isocyanate within a period of 30 seconds to 60 minutes, preferably 60 seconds to 50 minutes, particularly preferably 2 minutes to 40 minutes, following the separation of the crude product 1 in step (ii) into the product streams 2 and 3, in the present exemplary description for TDI, and the temperature of the product stream 2 is always maintained below or equal to 250° C., preferably between 100° C. and 250° C., particularly preferably between 120° C. and 230° C. The lower limit of said period is on the one hand governed by the spatial distance between reaction and workup, preferably distillation, and on the other hand, of course, by the fact that a minimum residence time in the selected separating device, preferably a distillation column, is necessary to remove the low-boiling substances mentioned.

The removal of the low boilers, the hydrogen chloride and the phosgene shall be carried out for the purposes of the invention if in each case at least 95.0% by weight, preferably at least 98.0% by weight, particularly preferably at least 99.0% by weight, especially preferably at least 99.5% by weight and exceptionally preferably 100% by weight of the low boilers, the hydrogen chloride and the phosgene are removed, based in each case on the weight of the low boilers, the weight of hydrogen chloride and the weight of the phosgene, which leaves the reaction chamber.

In a preferred embodiment of the workup in step (iii), said workup is carried out in more than one stage, wherein inert solvent, low boilers, hydrogen chloride and phosgene are removed from the product stream 2 by distillation in a first stage (iii.a), such that a product stream 4 depleted in inert solvent, low boilers, hydrogen chloride and phosgene is obtained, and in at least one further stage (iii.b) pure isocyanate 5 is obtained from the product stream 4 by distillation. These steps (iii.a) and (iii.b) may be carried out in apparatuses known from the prior art. It is only essential here that the low boilers, the hydrogen chloride and the phosgene in step (iii.a) are removed within a period of 30 seconds to 60 minutes, preferably 60 seconds to 50 minutes, particularly preferably 2 minutes to 40 minutes, following the separation of the crude product 1 in step (ii) into the product streams 2 and 3 and the temperature of the product stream 2 is always maintained below or equal to 250° C., preferably between 100° C. and 250° C., particularly preferably between 120° C. and 230° C. The dimensions and arrangement of the individual apparatuses, the sizes of connecting piping and flow rates must therefore be coordinated, such that the period up to the removal of the low boilers, the hydrogen chloride and the phosgene is maintained in accordance with the invention. A person skilled in the art is able to determine suitable parameters in a simple manner, if required, simple preliminary experiments may be necessary for a given production system. A so-called dephosgenation column is used for step (iii.a). A distillation column or dividing wall column known to those skilled in the art is preferably used for step (iii.b) for final purification. To obtain maximum purity isocyanate, multiple distillation columns may also be used in which different column types may be combined. Suitable apparatus for carrying out the steps (iii.a) and (iii.b) are described, for example, in Ullmann's Encyclopedia of Industrial Chemistry (Johann Stichlmair; Distillation, 2. Equipment; published online 2010-04-15, DOI: 10.1002/14356007.o08_o01), EP 1 546 091 A1, U.S. Pat. No. 2,471,134 A, US 2003/0047438 A1, EP 1 371 633 A1, EP 1 371 634 A1, EP 1 413 571 A1, EP 2 210 873 A1, WO 2010/039972 A2, DE 19 23 214 A1, EP 1 475 367 B1. How such apparatus are to be basically operated is known to those skilled in the art.

In the preferred multi-stage workup in steps (iii.a) and (iii.b), the time span to be observed according to the invention between the separation of the crude product 1 into the liquid product stream 2 and the gaseous product stream 3 corresponds to the mean residence time of isocyanate formed in step (i) between the effluent of stream 2 from a device for separating liquid and gas phases (step (ii)) and the effluent of product stream 4 depleted in inert solvent, low boilers, hydrogen chloride and phosgene from the dephosgenation column (step (iii.a)). The device for separating liquid and gas phases may be integrated in the reactor from step (i), such that the time span to be observed according to the invention between the separation of the crude product 1 into the liquid product stream 2 and the gaseous product stream 3 corresponds to the mean residence time of isocyanate formed in step (i) between the effluent of stream 2 from the reactor and the effluent of product stream 4 depleted in inert solvent, low boilers, hydrogen chloride and phosgene from the dephosgenation column. In this variant, the invention therefore relates to a method in which step (iii.a) is carried out in a dephosgenation column and step (iii.b) is carried out in a column for final purification, and in which the residence time of isocyanate formed in step (i) after the separation of the crude product 1 in step (ii) up to the effluent of the product stream 4 depleted in inert solvent, low boilers, hydrogen chloride and phosgene from the dephosgenation column in step (iii.a) is 30 seconds to 60 minutes, preferably 60 seconds to 50 minutes, particularly preferably 2 minutes to 40 minutes.

In this manner, a liquid product stream 4 depleted in inert solvent, low boilers, hydrogen chloride and phosgene is obtained. Stream 4 preferably comprises 40% by weight to 100% by weight, particularly preferably 60% by weight to 100% by weight, especially preferably 70% by weight to 100% by weight of the desired isocyanate, in this exemplary description for TDI, based in each case on the total weight of this stream, 0.10% by weight to 10% by weight, preferably 0.50% by weight to 7.0% by weight, particularly preferably 1.0% by weight to 5.0% by weight of high boilers, 0% by weight to 60% by weight, particularly preferably 0% by weight to 40% by weight, especially preferably 0% by weight to 30% by weight of solvent, 0 ppm by weight to 1500 ppm by weight (0-2%), preferably 0 ppm by weight to 1200 ppm by weight (0-1.2%), particularly preferably 0 ppm by weight to 1000 ppm by weight (0-1%) of low boilers, 0 ppm by weight to 1000 ppm by weight, preferably 0 ppm by weight to 800 ppm by weight, particularly preferably 0 ppm by weight to 600 ppm by weight of phosgene, 0 ppm by weight to 1000 ppm by weight, preferably 0 ppm by weight to 800 ppm by weight, particularly preferably 0 ppm by weight to 600 ppm by weight of hydrogen chloride.

This stream 4 is subsequently further processed by distillation in order to obtain pure isocyanate 5, in the present exemplary description for pure TDI. This purifying distillation may be conducted by all types known from the prior art. Examples are described, for example, in EP 1 371 634 A1 or the literature references or applications cited therein.

In the embodiment described above by way of example, toluylene diisocyanate (TDI) is obtained as product, in which the isomeric distribution substantially corresponds to that of the toluylene diamine used.

If other amines are reacted to the corresponding isocyanates, modifications are optionally carried out to the individual method details described above, which is a routine operation, however, to those skilled in the art.

By the inventive limitation of the temperature and the time period between the separation of the crude product 1 into the product streams 2 and 3 in stop (ii) and the removal of the low boilers, the hydrogen chloride and the phosgene from the desired isocyanate in step (iii), the thermally induced formation of carbodiimides on the one hand and the formation of secondary components having chloroformamidine-N-carbonyl chloride structural elements on the other hand is largely avoided. Such secondary components could otherwise lead to yield losses and/or quality issues and/or phosgene development in virtually phosgene-free method phases. The method according to the invention thus reduces yield losses and therefore economic disadvantages to a minimum.

EXAMPLES

The following examples demonstrate the importance of the removal of low boilers, hydrogen chloride and phosgene within the time period according to the invention. To demonstrate the importance of these parameters, the content of chemically bound phosgene was determined in all isocyanate samples. "Chemically bound" is, for example, phosgene present in carbodiimides. The greater the content of chemically bound phosgene in a crude isocyanate stream, the less selective is the reaction of the amine and the greater is the risk that phosgene is "kidnapped" into phosgene-free phases of the method.

In all examples, a mixture of 80% 2,4-TDA and 20% 2,6-TDA was phosgenated in each case in a gas phase method as described in EP 0 570 799 B1 (step (i)).

The crude product 1 was separated in a reaction quench zone into a liquid product stream 2 and a gaseous product stream 3 by injection of ortho-dichlorobenzene (ODB) as inert solvent (step (ii)).

The liquid reactor effluent 2 thus obtained comprised 87 ppm by weight (0.0087% by weight) chemically bound phosgene. To determine the content of chemically bound phosgene the following procedure was followed in all examples:

All samples were initially freed from the presence of potential residual amounts of dissolved phosgene by purging with dry nitrogen (40 l/h) for 8 hours at a maximum of 30° C. 200 g of the samples thus prepared were then heated for 30 min at 180° C. with stirring in a round-bottomed flask equipped with gas inlet line and reflux condenser and maintained for a further 90 min at this temperature with stirring. A nitrogen flow of 10 l/h was passed through the crude product solution throughout the entire experimental run in order to expel chemically bound phosgene subsequently liberated by thermal stress from the solution and to convey it to a cascade of wash bottles comprising methanol in defined amounts. Phosgene reacts with the methanol to give dimethyl carbonate, which can be analyzed quantitatively by gas chromatography (GC). For precise quantification, benzophenone was added to the methanol as internal standard for the GC analysis.

Example 1

Inventive

A sample of the liquid reactor effluent 2 was transferred continuously to a dephosgenation column and freed from inert solvent, low boilers, hydrogen chloride and phosgene (step (iii.a)), wherein a pre-purified isocyanate stream 4 was obtained as bottom product from the dephosgenation column
Temperature of the stream 2 on entering the dephosgenation column

163° C.

Temperature at the bottom of the dephosgenation column: 180° C.
Absolute pressure at the head of the dephosgenation column: 680 mbar The mean residence time between effluent of stream 2 from the reactor and effluent of stream 4 from the bottom of the dephosgenation column was ca. 20 min. Based on TDI, stream 4 contained 58 ppm by weight (0.0058% by weight) of chemically bound phosgene. This example shows that at a residence time in accordance with the invention between obtaining the liquid product stream 2 and the removal of the low boilers, the phosgene and the hydrogen chloride, the content of chemically bound phosgene is practically unchanged (the nominal value was even lower, due to measurement variations).

Example 2

Comparative Example

A further sample of the liquid reactor effluent 2 was treated under continuous feed of phosgene for 3 h at 180° C. and standard pressure, to recreate the conditions of a non-inventive residence time between obtaining the stream 2 and removal of the low boilers, the phosgene and the hydrogen chloride as realistically as possible.

Based on TDI, the sample contained 485 ppm by weight (0.0485% by weight) of chemically bound phosgene.

The examples demonstrate that the content of chemically bound phosgene in the inventive procedure is not adversely affected while at a larger residence time between obtaining the stream 2 and removal of the low boilers, the phosgene and the hydrogen chloride, the content of chemically bound phosgene significantly increases.

What is claimed is:
1. A continuous method for preparing an isocyanate by
   (i) reacting the corresponding primary amine with phosgene in stoichiometric excess in a reaction chamber, wherein the reaction is carded out either in the liquid phase in the presence of an inert solvent or in the gas phase, wherein a stream comprising a liquid inert solvent is added to the process product after leaving the reaction chamber,
   such that a crude product 1 is obtained comprising the desired isocyanate, inert solvent, secondary components having a boiling point below that of the isocyanate (low boilers), secondary components having a boiling point above that of the isocyanate (high boilers), hydrogen chloride and unreacted phosgene,
   (ii) separating the crude product 1 into a liquid product stream 2 containing the desired isocyanate and into a gaseous product stream 3,
   (iii) working-up the liquid product stream 2, wherein inert solvent, low boilers, high boilers, hydrogen chloride and phosgene are removed from the desired isocyanate, characterized in that
the low boilers, the hydrogen chloride and the phosgene are removed in step (iii) within a period of 30 second to 60 minutes following the separation of the crude product 1 in step (ii) into the product streams 2 and 3, and the temperature of the product stream 2 is always maintained below or equal to 250° C.

2. The method as claimed in claim 1, in which the workup step (iii) is carried out in more than one stage, wherein inert solvent, low boilers, hydrogen chloride and phosgene are removed from the product stream 2 by distillation in a first stage (iii.a), such that a product stream 4 depleted in inert solvent, low boilers, hydrogen chloride and phosgene is obtained, and in at least one further stage (iii.b) pure isocyanate 5 is obtained from the product stream 4 by distillation.

3. The method as claimed in claim 2, in which step (iii.a) is carried out in a dephosgenation column and step (iii.b) is carried out in a column for final purification, and in which the residence time of isocyanate formed in step (i) after the separation of the crude product 1 in step (ii) up to the effluent of the product stream 4 depleted in inert solvent, low boilers, hydrogen chloride and phosgene from the dephosgenation column in step (iii.a) is 30 seconds to 60 minutes.

4. The method as claimed in any of claims 1 to 3, in which the reaction of the primary amine with phosgene in the reaction chamber in step (i) is carried out in the gas phase.

5. The method of claim 1, in which the primary amine used is toluylenediamine.

6. A continuous method for preparing an isocyanate by
   (i) reacting the corresponding primary amine with phosgene in stoichiometric excess in a reaction chamber, wherein the reaction is carried out in the gas phase, wherein a stream comprising a liquid inert solvent is added to the process product after leaving the reaction chamber,
   such that a crude product 1 is obtained comprising the desired isocyanate, inert solvent, secondary components having a boiling point below that of the isocyanate (low boilers), secondary components having a boiling point above that of the isocyanate (high boilers), hydrogen chloride and unreacted phosgene,
   (ii) separating the crude product 1 into a liquid product stream 2 containing the desired isocyanate and into a gaseous product stream 3,
   (iii) working-up the liquid product stream 2, wherein inert solvent, low boilers, high boilers, hydrogen chloride and phosgene are removed from the desired isocyanate,
characterized in that
the low boilers, the hydrogen chloride and the phosgene are removed in step (iii) within a period of 30 second to 60 minutes following the separation of the crude product 1 in step (ii) into the product streams 2 and 3, and the temperature of the product stream 2 is always maintained below or equal to 250° C.

7. The method of claim 6, in which the workup step (iii) is carried out in more than one stage, wherein inert solvent, low boilers, hydrogen chloride and phosgene are removed from the product stream 2 by distillation in a first stage (iii.a), such that a product stream 4 depleted in inert solvent, low boilers, hydrogen chloride and phosgene is obtained, and in at least one further stage (iii.b) pure isocyanate 5 is obtained from the product stream 4 by distillation.

8. The method of claim 7, in which step (iii.a) is carried out in a dephosgenation column and step (iii.b) is carried out in a column for final purification, and in which the residence time of isocyanate formed in step (i) after the separation of the crude product 1 in step (ii) up to the effluent of the product stream 4 depleted in inert solvent, low boilers, hydrogen chloride and phosgene from the dephosgenation column in step (iii.a) is 30 seconds to 60 minutes.

9. The method of claim 6, in which the primary amine used is toluylenediamine.

* * * * *